US009329152B2

(12) United States Patent
Walker et al.

(10) Patent No.: US 9,329,152 B2
(45) Date of Patent: May 3, 2016

(54) GAS MAGNETOMETER

(75) Inventors: Thad Gilbert Walker, Madison, WI (US); Brian Robert Lancor, Madison, WI (US); Robert Wyllie, Silver Spring, MD (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1070 days.

(21) Appl. No.: 13/436,183

(22) Filed: Mar. 30, 2012

(65) Prior Publication Data

US 2013/0033255 A1 Feb. 7, 2013

Related U.S. Application Data

(63) Continuation-in-part of application No. 13/198,940, filed on Aug. 5, 2011, now Pat. No. 8,698,493.

(51) Int. Cl.
| | |
|---|---|
| *G01V 3/00* | (2006.01) |
| *G01N 27/74* | (2006.01) |
| *G01R 33/02* | (2006.01) |

(52) U.S. Cl.
CPC ............... *G01N 27/74* (2013.01); *G01R 33/02* (2013.01)

(58) Field of Classification Search
CPC ...................................................... G01R 33/02
USPC ....................................................... 324/304
See application file for complete search history.

(56) References Cited

U.S. PATENT DOCUMENTS

| | | | | |
|---|---|---|---|---|
| 8,587,304 | B2 * | 11/2013 | Budker et al. | 324/304 |
| 8,698,493 | B2 * | 4/2014 | Walker et al. | 324/307 |
| 8,994,371 | B2 * | 3/2015 | Larsen et al. | 324/304 |

OTHER PUBLICATIONS

Nelson, I.A, et al., Spin-Exchange Optical Pumping Using a Frequency-Narrowed High Power Diode Laser, Applied Physics Letters, vol. 76, No. 11, Mar. 13, 2000, pp. 1356-1358, The American Institute of Physics.
Walter, D.K., et al. Estimates of the Relative Magnitudes of the Isotropic and Anisotropic Magnetic-Dipole Hyperfine Interactions in Alkali-Metal-Noble-Gas Systems, Physical Review A, vol. 58, No. 5, Nov. 1998, pp. 3642-3653, The American Physical Society.
Sukenic, C.I., et al., Role of Spontaneous Emission in Ultracold Two-Color Optical Collisions, Physical Review A, vol. 59, No. 1, Jan. 1999, pp. 889-892, The American Physical Society.
Leo, Paul J., et al., Elastic and Inelastic Collisions of Cold Spin-Polarized 133Cs Atoms, Physical Review Letters, vol. 81, No. 7, Aug. 17, 1998, pp. 1389-1392, The American Physical Society.
Williamson III, R.S., et al., A Magneto-Optical Trap Loaded From a Pyramidal Funnel, Optics Express, vol. 3, No. 3, Aug. 3, 1998, pp. 111-117, OSA.
Kadlecek, S., et al., Field Dependence of Spin Relaxation in a Dense Rb Vapor, Physical Review Letters, vol. 80, No. 25, Jun. 22, 1998, pp. 5512-5515, The American Physical Society.

(Continued)

*Primary Examiner* — Louis Arana
(74) *Attorney, Agent, or Firm* — Boyle Fredrickson, S.C.

(57) ABSTRACT

Measurement of a precessional rate of a gas, such as an alkali gas, in a magnetic field is made by promoting a non-uniform precession of the gas in which substantially no net magnetic field affects the gas during a majority of the precession cycle. This allows sensitive gases that would be subject to spin-exchange collision de-phasing to be effectively used for extremely sensitive measurements in the presence of an environmental magnetic field such as the Earth's magnetic field.

19 Claims, 8 Drawing Sheets

(56) References Cited

OTHER PUBLICATIONS

Sukenik, C.I., et al., Low Saturation Instensities in Two-Photon Ultracold Collisions, Physical Review Letters, vol. 81, No. 4, Jul. 27, 1998, pp. 782-785, The American Physical Society.

Kadlecek, Stephen, et al., Measurement of Potassium-Potassium Spin Relaxation Cross Sections, Nuclear Instruments and Methods in Physics Research A 402 (1998), pp. 208-211, Elsevier Science B.V.

Thywissen, Joseph H., Spin-Rotation Interaction of Alkali-Metal-He-Atom Pairs, Physical Review A, vol. 56, No. 3, Sep. 1997, pp. 2090-2094, The American Physical Society.

Schappe, R.S., Absolute Electron-Impact Ionization Cross Section Measurements Using a Magneto-Optical Trap, Physical Review Letters, vol. 76, No. 23, Jun. 3, 1996, pp. 4328-4331, The American Physical Society.

Walker, Thad G., et al., Spin-Exchange Optical Pumping of Noble-Gas Nuclei, Reviews of Modern Physics, vol. 69, No. 2, Apr. 1997, pp. 629-642, The American Physical Society.

Hoffmann, D., et al., Trap-Depth Measurements Using Ultracold Collisions, Physical Review A, vol. 54, No. 2, Aug. 1996, pp. R1030-R1033, The American Physical Society.

Bali, S., et al. Measurements of Intensity Correlations of Scattered Light from Laser-Cooled Atoms, Physical Review A, vol. 53, No. 5, May 1996, pp. 3469-3472, The American Physical Society.

Nesnidal, Renee C., et al., Multilayer Dielectric Structure for Enhancement of Evanescent Waves, Applied Optics, vol. 35, No. 13, May 1, 1996, pp. 2226-2229, Optical Society of America.

Williamson III, R.S., et al., Magneto-Optical Trapping and Ultracold Collisions of Potassium Atoms, J. Opt. Soc. Am. B, vol. 12, No. 8, Aug. 1995, pp. 1393-1397, Optical Society of America.

Feng, Paul, et al., Inexpensive Diode Laser Microwave Modulation for Atom Trapping, Am. J. Phys. 63 (10), Oct. 1995, pp. 905-908, American Association of Physics Teachers.

Anderson, L.W., et al., Spin Exchange Optical Pumping of Hydrogen and Deuterium Nuclei, Nuclear Instruments and Methods in Physics Research A 357 (1995), pp. 220-224, Elsevier Science B.V.

Walker, T., et al., Effects of Hyperfine Structure on Alkali Trap-Loss Collisions, Laser Physics, vol. 4, No. 5 (1994), pp. 1085-1092.

Schappe, R.S., et al., Electron Collision Cross-Sections Measured with the Use of a Magneto-Optical Trap, Europhysics Letters 29 (6), Feb. 20, 1995, pp. 439-444, Les Editions de Physique.

Walker, Thad, Three-Dimensional Analytical Calculation of the Magneto-Optical Trapping Forces on a Stationary J=0 → J=1 Atom, Mar. 16, 1998, pp. 1-7.

Peters, M.G., et al., Laser-Induced Ultracold Rb(5S1/2) + Rb(5P1/2) Collisions, Physical Review A, vol. 50, No. 2, Aug. 1994, pp. R906-R909, The American Physical Society.

Bali, S., et al., Novel Intensity Dependence of Ultracold Collisions Involving Repulsive States, Europhysics Letters 27 (4), Aug. 1, 1994, pp. 273-277.

Hoffman, D., et al., Measurements of Rb Trap-Loss Collision Spectra, Journal of the Optical Society of America B, (1994), pp. 712-720, Optical Society of America.

Martin, Cody, et al., Laser Optical Pumping of Potassium in a High Magnetic Field Using Linearly Polarized Light, Nuclear Instruments and Methods in Physics Research A 335 (1993), pp. 233-238, Elsevier Science Publishers B.V.

Walker, T., et al., Spin-Exchange Collisions and Their Consequences for Spin-Polarized Gas Targets of Hydrogen and Deuterium, Nuclear Instruments and Methods in Physics Research A 334 (1993), pp. 313-324, Elsevier Science Publishers B.V.

Walker, T., et al., Consequences of Spin-Exchange Collisions for Polarized Hydrogen and Deuterium Targets, Physical Review Letters, vol. 71, No. 14, Oct. 4, 1993, The American Physical Society.

Feng, Paul, et al., Comparison of Trap-Loss Collision Spectra for 85Rb and 87Rb, Physical Review A, vol. 47, No. 5, May 1993, The American Physical Society.

Hoffmann, D., et al., Excited-State Collisions of Trapped 85Rb Atoms, Physical Review Letters, vol. 69, No. 5, Aug. 3, 1992, pp. 753-756, The American Physical Society.

Walker, T., et al., Spin-Polarized Spontaneous-Force Atom Trap, Physical Review Letters, vol. 69, No. 15, Oct. 12, 1992, pp. 2168-2172, The American Physical Society.

Anderson, L.W., et al., The Effect of Radiation Trapping on a High Field Spin Exchange Optically Pumped Target, Nuclear Instruments and Methods in Physics Research A316 (1993), pp. 123-127, Elsevier Science Publishers B.V.

Walker, T., et al., A Vortex-Force Atom Trap, Physical Letters A 163 (1992), pp. 309-312, Elsevier Science Publishers B.V.

Sesko, D.W., et al., Behavior of Neutral Atoms in a Spontaneous Force Trap, J. Opt. Soc. Am. B, vol. 8, No. 5, May 1991, pp. 946-958, Optical Society of America.

Walker, Thad, et al., Collective Behavior of Optically Trapped Neutral Atoms, Physical Review Letters, vol. 64, No. 4, Jan. 22, 1990, pp. 408-412, The American Physical Society.

Walker, Thad G., Estimates of Spin-Exchange Parameters for Alkali-Metal—Noble-Gas Pairs, Physical Review A, vol. 40, No. 9, Nov. 1, 1989, pp. 4959-4964, The American Physical Society.

Sesko, D., et al., Collisional Losses from a Light-Force Atom Trap, Physical Review Letters, vol. 63, No. 9, Aug. 28, 1989, pp. 961-964, The American Physical Society.

Schaefer, S.R., et al., Frequency Shifts of the Magnetic-Resonance Spectrum of Mixtures of Nuclear Spin—Polarized Noble Gases and Vapors of Spin-Polarized Alkali-Metal Atoms, Physical Review A, vol. 39, No. 11, Jun. 1, 1989, pp. 5613-5623, The American Physical Society.

Walker, T.G., et al., Deexcitation of Metastable Ba+, J. Chem. Phys. 89 (3), Aug. 1, 1998, pp. 1358-1363, The American Institute of Physics.

Bonin, K.D., et al., Relaxation of Gaseous Spin-Polarized 3He Targets due to Ionizing Radiation, Physical Review A, vol. 37, No. 9, May 1, 1988, pp. 3270-3282, The American Physical Society.

Walker, T.G., et al., Modulation Technique for Measuring Diffusion Coefficients of Ba in Noble Gases, J. Chem. Phys. 87 (1), Jul. 1, 1987, pp. 660-663, The American Institute of Physics.

Happer, W., et al., The Stability of Spin-Polarized Nitrogen Crystals, Chemical Physics Letters, vol. 135, No. 4,5, Apr. 10, 1987, pp. 451-453, Elsevier Science Publishers B.V.

Walker, T.G., et al., Electron—Noble-Gas Spin-Flip Scattering at Low Energy, Physical Review A, vol. 35, No. 9, May 1, 1987, pp. 3749-3752, The American Physical Society.

Happer, W., et al., The Spin-Rotation Interaction of Atoms with Half-Filled Electrons Shells, Physics Letters A, vol. 120, No. 6, Mar. 2, 1987, pp. 293-295, Elsevier Science Publishers B.V.

Mokhtari, A., et al., Analyzing Powers in $\pi+p$ Elastic Scattering at Intermediate Energies, Physical Review Letters, vol. 55, No. 4, Jul. 22, 1985, pp. 359-362, The American Physical Society.

Huennekens, J., et al., Near-Infrared Spectra of the Nak Molecule, J. Chem. Phys. 83 (10), Nov. 15, 1985, pp. 4949-4957, The American Institute of Physics.

Wu, Z., et al., Spin-Rotation Interaction of Noble-Gas Alkali-Metal Atom Pairs, Physical Review Letters, vol. 54, No. 17, Apr. 29, 1985, pp. 1921-1924, The American Physical Society.

Huennekens, J., et al., Ionization, Excitation of High-Lying Atomic States, and Molecular Flourescence in Cs Vapor Excited at $\lambda=455.7$ and 459.4 nm, Physical Review A, vol. 31, No. 1, Jan. 1985, pp. 196-209, The American Physical Society.

Brahms, N., et al., Formation of Van Der Waals Molecules in Buffer-Gas-Cooled Magnetic Traps, Physical Review Letters, PRL 105, 03301, Jul. 16, 2010, pp. 1-4, The American Physical Society.

Saffman, M., et al., Quantum Infomation with Rydberg Atoms, Reviews of Modern Physics, vol. 82, Aug. 18, 2010, pp. 2313-2363, The American Physical Society.

Schwarzschild, Bertram, Experiments Show Blockading Interaction of Rydberg Atoms Over Long Distances, Physics Today, Feb. 2009, pp. 15-18, American Institute of Physics.

Miller, Johanna, Neutral Atoms are Entangled in Hyperfine States via Rydberg Blockade, Physics Today, Feb. 2010, pp. 13-17.

Saffman, M., et al., Rydberg State Mediated Quantum Gates and Entanglement of Pairs of Neutral Atoms, 22nd International Conference on Atomic Physics, Journal of Physics: Confeence Series 264 (2011) 012023, pp. 1-8, IOP Publishing.

(56) References Cited

OTHER PUBLICATIONS

Brahms, Nathan, et al., Formation and Dynamics of Van Der Waals Molecules in Buffer-Gas Traps, Owner Societies 2011, Phys. Chem. Chem. Phys., Aug. 1, 2011, pp. 1-17.

Lancor, B., et al., Polarization Limits in K-Rb Spin-Exchange Mixtures, Physical Review A 83, 065401, Jun. 27, 2011, pp. 1-3, American Physical Society.

Babcock, E., et al., Effects of High Intensity Neutron Flux on In-Situ Spin-Exchange Optical Pumping of 3He, JCNS Workshop on Modern Trends in Production and Applications of Polarized 3He, Journal of Physics: Conference Series 294 (2011) 012011, pp. 1-9, IOP Publishing.

Lancor, B., et al., Effects of Nitrogen Quenching Gas on Spin-Exchange Optical Pumping of 3He, Physical Review A82, 043417 (2010), Oct. 18, 2010, pp. 1-7.

Walker, Thad G., Fundamentals of Spin-Exchange Optical Pumping, JCNS Workshop on Modern Trends in Production and Applications of Polarized 3He, Journal of Physics: Conference Series 294 (2011) 012001, pp. 1-8, IOP Publishing Ltd.

Lancor, B., et al., Circular Dichroism of RbHe and RbN2 Molecules, Physical Review A 82, 043435 (2010), Oct. 27, 2010, pp. 1-11, The American Physical Society.

Zhang, X.L., et al., Deterministic Entanglement of Two Neutral Atoms Via Rydberg Blockade, Physical Review A82, 030306(R) (2010), Sep. 29, 2010, pp. 1-4, The American Physical Society.

Lancor, B., et al., Breakdown of Angular Momentum Selection Rules in High Pressure Optical Pumping Experiments, Physical Review Letters, Week Ending Aug. 20, 2010, pp. 1-4, The American Physical Society.

Isenhower, L., et al., Demonstration of a Neutral Atom Controlled-NOT Quantum Gate, Department of Physics, Physical Review Letters, Week Ending Jan. 8, 2010, pp. 1-4, The American Physical Society.

Walker, T.G., et al., Method for Deducing Anisotropic Spin-Exchange Rates, Physical Review A 81, 032709 (2010), Mar. 29, 2010, pp. 1-4, The American Physical Society.

Babcock, E., et al., Effects of High-Flux Neutron Beams on 3He Cells Polarized in Situ with Spin-Exchange Optical Pumping, Physical Review A 80, 033414, Sep. 17, 2009, pp. 1-18, The American Physical Society.

Brekke, E., et al., Four-Wave Mixing in Ultracold Atoms Using Intermediate Rydberg States, Physical Review A 78, 063830, Dec. 18, 2008, pp. 1-5, The American Physical Society.

Sharma, M., et al., Neutron Beam Effects on Spin-Exchange-Polarized 3He, Physical Review Letters, PRL 101, 083002, Aug. 20, 2008, pp. 1-5, The American Physical Society.

Urban, E., et al., Observation of Rydberg Blockade Between Two Atoms, Nature Physics, vol. 5, Feb. 2009, pp. 110-114.

Walker, Thad G., et al., Consequences of Zeeman Degeneracy for the Van Der Waals Blockade Between Rydberg Atoms, Physical Review A 77, 032723, Mar. 26, 2008, pp. 1-18, The American Physical Society.

Day, J.O., et al., Dynamics of Low-Density Ultracold Rydberg Gases, Physical Review A77, 052712, May 23, 2008, pp. 1-9, The American Physical Society.

Johnson, T.A., et al., Rabi Oscillations Between Ground and Rydberg States with Dipole-Dipole Atomic Interactions, Physical Review Letters, PRL 100, 113003, Mar. 19, 2008, pp. 1-4, The American Physical Society.

Walker, Thad G., et al., Comment on "MF-Dependent Lifetimes Due to Hyperfine Induced Interference Effects", Physical Review Letters, PRL 98, 269303, Jun. 28, 2009, pp. 1, The American Physical Society.

Bonessi, Douglas, et al., Optical Forces on Particles of Arbitrary Shape and Size, Journal of Optics A: Pure and Applied Optics, J. Opt. A: Pure Appln. Opt. 9 (2007), pp. S228-S234, IOP Publishing Ltd.

Li, Zhimin, et al., Parametric Modulation of an Atomic Magnetometer, Applied Physics Letters 89, 134105, Sep. 27, 2006, pp. 1-3, The American Institute of Physics.

Chen, W.C., et al., Spin-Exchange Optical Pumping of 3He with Rb-K Mixtures and Pure K, Physical Review A 75, 013416, Jan. 23, 2007, pp. 1-14, The American Physical Society.

Yavuz, D.D., et al., Fast Ground State Manipulation of Neutral Atoms in Microscopic Optical Traps, Physical Review Letters, PRL 96, 063001, Feb. 14, 2006, pp. 1-4, The American Physical Society.

Babcock, E., et al., Limits to the Polarization for Spin-Exchange Optical Pumping of 3He, Physical Review Letters, PRL 96, 083003, Mar. 3, 2006, pp. 1-4, The American Physical Society.

Saffman, M., et al., Analysis of a Quantum Logic Device Based on Dipole-Dipole Interactions of Optically Trapped Rydberg Atoms, Physical Review A 72, 022347, Aug. 31, 2005, pp. 1-21, The American Physical Society.

Babcock, Earl, et al., 3He Polarization-Dependent EPR Frequency Shifts of Alkali-Metal-3He Pairs, Physical Review A 71, 013414, Jan. 19, 2005, pp. 1-5, The American Physical Society.

Saffman, M., et al., Entangling Single- and N-Atom Qubits for Fast Quantum State Detection and Transmission, Physical Review A 72, 042302, Oct. 7, 2005, pp. 1-6, The American Physical Society.

Shelton, W. Andrew, et al., Nonlinear Motion of Optically Torqued Nanorods, Physical Review E 71, 036204, Mar. 11, 2005, pp. 1-8, The American Physical Society.

Sebby-Strabley, J., et al., High-Density Mesoscopic Atom Clouds in a Holographic Atom Trap, Physical Review A 71, 021401(R), Feb. 9, 2005, pp. 1-4, The American Physical Society.

Babcock, Earl, et al., Frequency-Narrowed Diode Array Bar, Applied Optics, vol. 44, No. 15, May 20, 2005, pp. 3098-3104, Optical Society of America.

Gentile, T.R., et al., Polarized 3He Spin Filters for Slow Neutron Physics, Journal of Research of the National Institute of Standards and Technology, vol. 110, No. 3, May-Jun. 2005, pp. 299-304.

Chann, B., et al., Production of Highly Polarized 3He Using Spectrally Narrowed Diode Laser Array Bars, Journal of Applied Physics, vol. 94, No. 10, Nov. 15, 2003, pp. 6908-6914, American Institute of Physics.

Walker, Thad G., et al., Zeros of Rydberg-Rydberg Föster Interactions, Journal of Physics B: Atomic, Molecular and Optical Physics 38, Jan. 5, 2005, pp. S309-S319, Institute of Physics Publishing.

Babcock, Earl, et al., Hybrid Spin-Exchange Optical Pumping of 3He, Physical Review Letters, vol. 91, No. 12, Sep. 16, 2003, pp. 1-4, The American Physical Society.

Newell, R., et al., Dense Atom Clouds in a Holographic Atom Trap, Optic Letters, vol. 28, No. 14, Jul. 15, 2003, pp. 1266-1268, Optical Society of America.

Saffman, M, et al., Creating Single-Atom and Single-Photon Sources from Entangled Atomic Ensembles, Physical Review A 66, 065403, Dec. 16, 2002, pp. 1-4, The American Physical Society.

Chann, B., et al., Skew Light Propagation in Optically Thick Optical Pumping Cells, Physical Review A, 66, 033406, Sep. 27, 2002, pp. 1-3, The American Physical Society.

Chann, B., et al., 129Xe-Xe Molecular Spin Relaxation, Physical Review Letters, vol. 88, No. 11, Mar. 18, 2002, pp. 1-4, The American Physical Society.

Bonin, Keith D., et al., Light Torque Nanocontrol, Nanomotors and Nanorockers, Optics Express 984, vol. 10, No. 19, Sep. 23, 2002, OSA.

Chann, B., et al., Measurements of 3He Spin-Exchange Rates, Physical Review A, 66, 032703, Sep. 13, 2002, pp. 1-9, The American Physical Society.

Nelson, I.A., et al., Rb-Xe Spin Relaxation in Dilute Xe Mixtures, Physical Review A, vol. 65, 012712, Dec. 14, 2001, pp. 1-6, The American Physical Society.

Kadlecek, S., et al., Spin Relaxation in Alkali-Metal $1\Sigma+g$ Dimers, Physical Review A, vol. 64, 052717, Oct. 15, 2001, pp. 1-11, The American Physical Society.

Wise, T., et al., Nuclear Polarization of Hydrogen Molecules from Recombination of Polarized Atoms, Physical Review Letters, vol. 87, No. 4, Jul. 23, 2001, pp. 1-4, The American Physical Society.

Kadlecek, S., et al., Spin-Axis Relaxation in Spin-Exchange Collisions of Alkali-Metal Atoms, Physical Review A, vol. 63, 052717, Apr. 18, 2001, pp. 1-5, The American Physical Society.

(56) References Cited

OTHER PUBLICATIONS

Vliegen, E., et al., Faraday Rotation Density Measurements of Optically Thick Alkali Metal Vapors, Nuclear Instruments and Methods in Physics Research A 460, Aug. 31, 2000, pp. 444-450, Elsevier Science B.V.

Kadlecek, S., et al., Nondestructive Spatial Heterodyne Imaging of Cold Atoms, Optics Letters, col. 26, No. 3, Feb. 1, 2001, pp. 137-139, Optical Society of America.

Erickson, C.J., et al., Spin Relaxation Resonances Due to the Spin-Axis Interaction in Dense Rubidium and Cesium Vapor, Physical Review Letters, vol. 85, No. 20, Nov. 13, 2000, pp. 4237-4240, The American Physical Society.

Chann, B., et al., Frequency-Narrowed External-Cavity Diode-Laser-Array Bar, Optics Letters, vol. 25, No. 18, Sep. 15, 2000, pp. 1352-1354, Optical Society of America.

Walker, Thad G., Holography Without Photography, Am. J. Phys. 67 (9), Sep. 1999, pp. 783-785, American Association of Physics Teachers.

Nesnidal, Renee C., et al., Light-Induced Ultracold Spin-Exchange Collisions, Physical Review A, vol. 62, 030701 (R), Aug. 18, 2000, pp. 1-4, The American Physical Society.

Pool, Robert, Making Atoms Jump Through Hoops, Research News, Science, New Series vol. 248, No. 4969, Jun. 1, 1990, pp. 1076-1078, American Association for the Advancement of Science.

Weidemuller, Matthias, There Can Be Only One, News & Views, Nature Physics, vol. 5, Feb. 2009, pp. 91-92, Macmillan Publishers Limited.

Donley, E.A., Nuclear Magnetic Resonance Gyroscopes, pp. 17-22, IEEE Sensors 2010 Conference, IEEE, Piscataway, NJ.

* cited by examiner

GAS MAGNETOMETER

CROSS REFERENCE TO RELATED APPLICATION

This application is a continuation in part on U.S. patent application Ser. No. 13/198,940 filed Aug. 5, 2011 now U.S. Pat. No. 8,698,493 and hereby incorporated by reference.

This invention was made under HD057965 awarded by the National Institutes of Health and DE-FC02-03ER46093 awarded by the U.S. Department of Energy. The government has certain rights in the invention.

BACKGROUND OF THE INVENTION

The present invention relates to a magnetometer that may be sensitive to very small magnetic fluctuations in the presence of a much larger static field, and in particular to a magnetometer that measures precession of gas atoms in a way that the dephasing effects between gas atoms are reduced.

Atoms such as the alkali metals have a net spin which possesses a magnetic moment. Accordingly, if such atoms can be polarized and stimulated into precession, the frequency of precession can be used to precisely measure a magnetic field free from other influences. In this way, a precision magnetometer may be constructed.

The ability of alkali gas atoms to measure magnetic field is often limited by interactions between the alkali gas atoms (spin-exchange relaxation) themselves which cause de-phasing of the precessing alkali gas atoms. These interactions can be reduced, by eliminating any environmental magnetic field other than the field being measured (for example the Earth's magnetic field), for example by using nulling coils energized to produce a canceling countervailing magnetic field. Such magnetometers are termed "spin exchange relaxation-free (SERF) magnetometers."

Nulling the external magnetic field can be difficult and must be extremely precise to obtain the benefits of increased sensitivity of the alkali gas atoms.

SUMMARY OF THE INVENTION

The present invention provides a magnetometer with high magnetic field sensitivity comparable to a SERF magnetometer without the need to operate in a near zero magnetic field. This is accomplished by modulating the precession of the alkali atoms with a controllable time-dependent magnetic field to produce a time averaged stationary magnetic moment. This modulation pattern may provide a modulating field having extremely narrow pulses during which precession occurs and a long intervening duration during which precession is frozen. In this latter state, the atoms are inherently retained in a low magnetic field in which spin exchange collisions do not dephase the magnetic moments of the atoms. The modulation signal may be controlled by a feedback mechanism that largely eliminates requirements for precise pulse shaping or pulse amplitude. In this way, the problems attendant to nulling the external magnetic field with a static field are largely eliminated.

Specifically, the present invention provides a magnetometer having a chamber holding a gas exposable to an external magnetic field and directed along a z-axis. An electromagnet is positioned to apply a local magnetic field to the chamber and a signal source communicating with the electromagnet generates a field signal adapted to drive the electromagnet to produce a local magnetic field causing a non-uniform precession of a magnetic moment of the gas at an average frequency substantially equal to a frequency of uniform precession of the gas in the external magnetic field without an influence of the local magnetic field, while limiting a portion of each precession cycle during which substantial precession occurs. A monitor outputs a signal indicating the precession of the gas.

It is thus an object of at least one embodiment of the invention to provide a high sensitivity magnetometer that may operate in ambient magnetic field that might normally cause substantial spin exchange collision dephasing.

The signal may be adapted to limit the portion of each precession cycle during which substantial precession occurs to less than 50% of the precession cycle, or to less than 10% of the precession cycle.

It is thus an object of at least one embodiment of the invention to substantially minimize the effect of spin exchange collisions on dephasing of the precession of the atoms.

The magnetometer may further include a precession monitor providing a moment signal indicating orientation of a magnetic moment of the gas in the chamber and a feedback control system receiving the moment signal to control a shape of the field signal from the signal source to complete substantially 360 degrees of precession of the gas during the portion of each precession cycle during which substantial precession occurs.

It is thus an object of at least one embodiment of the invention to provide a feedback control mechanism eliminating the need for precise open-loop wave shaping and/or amplitude control.

The feedback control system may monitor a phase of the moment signal to control the duration of portions of the field signal during which substantial precession occurs.

It is thus an object of at least one embodiment of the invention to provide a simple control strategy for adjusting the field signal largely indifferent to the exact field signal shape or amplitude.

Alternatively or in addition, the feedback control system may receive the moment signal to control a frequency of the signal from the signal source to produce an average signal value of substantially zero.

It is thus an object of at least one embodiment of the invention to provide a feedback mechanism conforming the non-uniform precession of the atoms to their natural precession in the absence of the local field.

The feedback control system may monitor an average value of the moment signal to control the frequency of the field signal.

It is thus an object of at least one embodiment of the invention to provide a simple technique for frequency control.

These particular objects and advantages may apply to only some embodiments falling within the claims and thus do not define the scope of the invention.

DETAILED DESCRIPTION OF THE PREFERRED EMBODIMENT

Noble Gas Resonator

Figure 1:
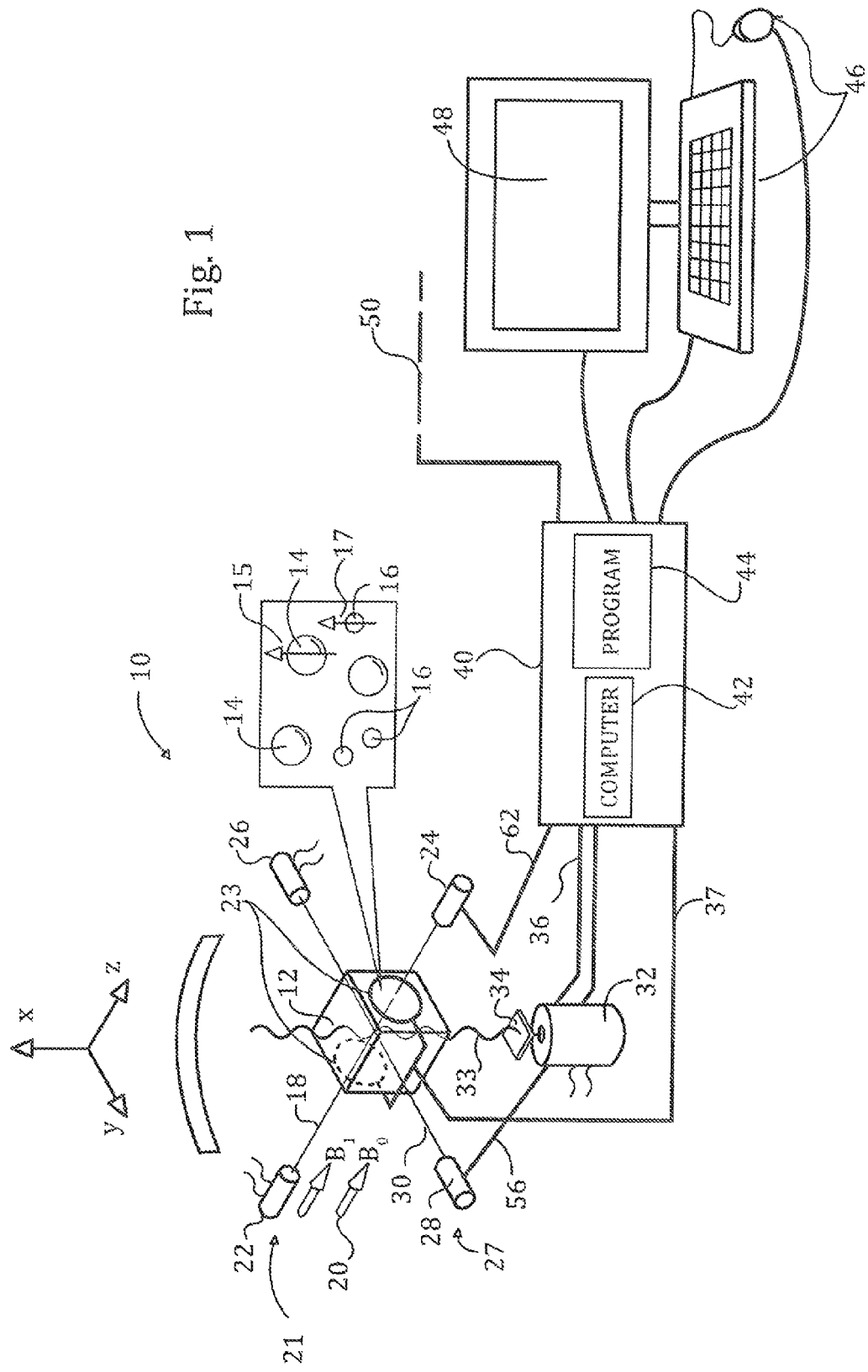
FIG. 1 is a simplified perspective view of a magnetic resonator system described in the parent application to this continuation application invention and using a noble gas and showing orientation of a stimulating laser, magnetic field coils, and orthogonal sensing lasers about a gas chamber holding a noble gas and alkali gas.

Referring now to FIG. 1, a magnetic resonator system 10, described generally in co-pending application Ser. No. 11/198,940 filed Aug. 5, 2011 may include a chamber 12 holding an alkali gas 14 and noble gas 16. In one embodiment, the alkali gas 14 may be rubidium (Rb) and the noble gas 16 may be a helium isotope (3-He). Each of the atoms of the alkali gas 14 and the noble gas 16 has magnetic moments 15 and 17, respectively, represented by directional arrows in the figure.

The chamber 12 may have transparent walls allowing a laser beam 18 of a first Faraday rotational probe 21 to pass through the chamber 12 along a z-axis of a Cartesian coordinate system having its z-axis aligned with an external magnetic field 20 ($B_0$). This laser beam 18 may be emitted from a laser source 22 and received by a polarimeter 24 positioned on opposite sides of the chamber 12 along the z-axis from the laser source 22. As will be understood in the art, this first Faraday rotational probe 21 provides a measure of a z-axis component of the magnetic moment 15 of the population of alkali gas 14.

A set of magnetic coils 23 (for example a Helmholtz coil pair flanking the chamber and aligned along the z-axis) may provide an alternating or pulsed magnetic field ($B_1$) aligned along the z-axis. As will be discussed below, this field provides a means for controlling the time-averaged alkali spin precession in the presence of an external field $B_0$. In particular, the field $B_1$ will be modulated to moderate the naturally fast precession rate of the alkali gas 14 in the external magnetic field $B_0$ to be aligned along the pump laser 32 direction.

A second Faraday rotational probe 27 may include a laser source 26 directing a laser beam 30 along the y-axis through the chamber 12 to a corresponding receiving polarimeter 28 on the other side of the chamber 12. This second Faraday rotational probe 27 provides a measure of the y-axis component of the magnetic moment 15 of the population of alkali gas 14.

A "pump" laser 32 may direct a laser beam 33 along the x-axis through the chamber 12 after passing through a polarization modulator 34. The pump laser 32 and polarization modulator 34 may "spin-polarize" the magnetic moment 15 of the alkali gas 14 to align in either of two directions along the x-axis (upward or downward as depicted) according to a modulation signal 36 received by the polarization modulator 34. This polarization occurs by transfer of the angular momentum of the polarized photons of the laser beam 33 to the alkali gas 14 as will be generally understood in the art.

It will be understood that the various laser sources 22, 26, and 32 in various combinations may be derived from one or more light sources.

Signals from the polarimeters 28 and 24 may be provided as electrical signal input to a control system 40 to be processed as will be described below. The control system 40 may in turn output the modulation signal 36 to the polarization modulator 34. The control system 40 may also output the modulation signal 37 to the magnetic coils 23. The control system 40 may be constructed of discrete components or functional blocks such as lock-in amplifiers, frequency counters and the like as will be described below or these elements may be implemented in software in an electronic computer 42 as depicted, or in dedicated hardware including an application-specific integrated circuit or digital signal processor, or as a combination of different elements in a hybrid configuration. In the case of implementation in a computer 42, the computer 42 may execute a stored program 44 and may communicate with user input devices 46 such as a keyboard and/or mouse and may provide output for example through a graphic display screen 48 or other functionally similar device. Alternatively, or in addition, the control system 40 may provide a control output 50, for example, providing a gyro output (e.g., angle or angular rate about the z-axis) or a magnetometer output (e.g. Gauss) use for control of an ancillary device such as aircraft or the like.

Figure 2:
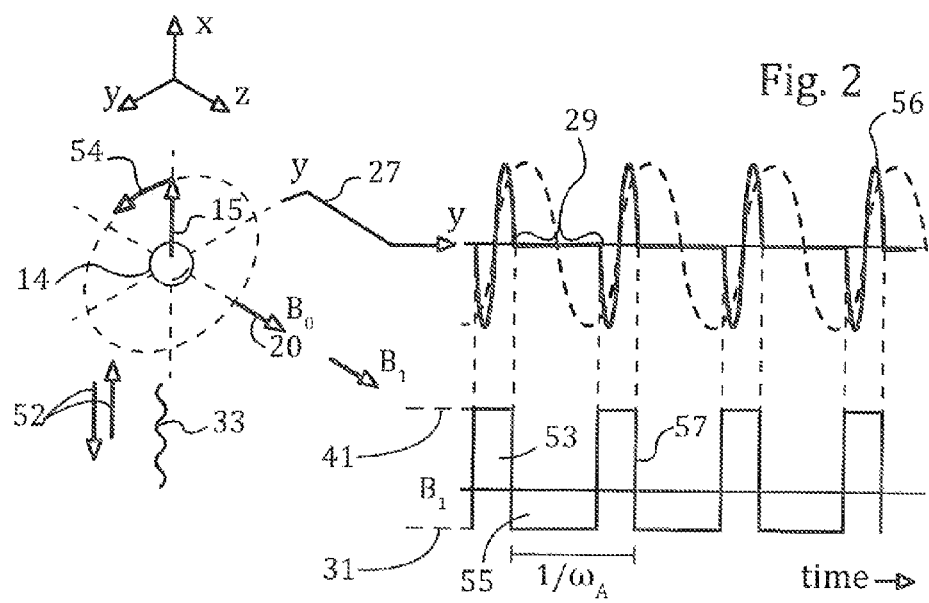
FIG. 2 is a simplified perspective view of the precession of the magnetic moment of the atoms of the alkali gas stimulated into precession in the x-y plane at a changing precession rate plotted against time and showing the driving magnetic field signal for this nonuniform precession.

Referring also to FIG. 2, during operation of the magnetic resonator system 10, the control system 40 will control the laser beam 33 and the applied magnetic field $B_1$ to drive the magnetic moment of the population of alkali gas 14 into precession substantially within the x-y plane. This precession is invoked by illuminating the alkali gas 14 with photons having alternate upward and downward angular momentum indicated by arrows 52. The momentum of the photons is then transferred to the alkali gas 14 to align the magnetic moment 15 of the alkali gas 14 with the photon angular momentums. Ongoing precession of the alkali gas 14 is then controlled by varying the $B_1$ field by control signal 37. The y-axis component of this precession of the magnetic moment 15 of the alkali gas 14 may be detected by the beam 30 of the second Faraday rotational probe 27

Control of the $B_1$ will be such that the precession 54 of the magnetic moment 15 of the alkali gas 14 in the x-y plane will not be at a uniform angular rate such as would be detected as a sinusoidal waveform by the second Faraday rotational probe 27, but rather, as an irregular angular rate, progressing relatively slower in the upper half cycle such as will produce a compressed precession waveform 56. The compressed precession waveform 56 represents the y-axis component of the magnetic moment 15 precessing at an irregular rate having a greater dwell time 29 when the magnetic moment of the alkali gas 14 is facing in an upward rather than the downward direction.

This compressed precession waveform 56 may be produced by modulating the $B_1$ field to a low relatively constant negative value 31 to substantially offset the $B_0$ field during the time 29 (greatly reducing the precession when the magnetic moment 15 is facing upward) for most of the period $1/\omega$ of the normal precession of the alkali gas 14 in field $B_0$ The field $B_1$ may then be maximized during a short time remaining in $2\pi/\omega$ by providing a positive pulse of amplitude 41 augmenting the field $B_0$ to promote rapid precession of the alkali gas 14 by 360 degrees back to the upward orientation. The field $B_1$ is controlled to have no direct current (that is areas 53 and 55 during times 29 and the remainder of $1/\omega$ are equal and opposite) so that it has no average effect on the precession frequency of the alkali gas 14 or noble gas 16.

Figure 3:
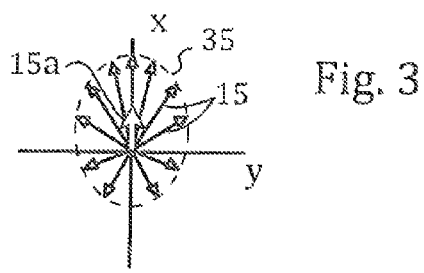
FIG. 3 is a vector diagram showing orientation of the magnetic moment of the alkali gas in the x-y plane as weighted by incremental dwell time at each angle, per the time plot of FIG. 13, illustrating a magnetic moment of the alkali gas having a time averaged upward vertical orientation.

Referring momentarily to FIG. 3, a diagram of the alkali magnetic moment 15 at various points in time as an angular vector having a length proportional to the incremental dwell time at each angle, it traces an oval outline 35 reflecting the increased time weighting of the magnetic moment in the upward direction. The centroid of this outline 35 may illustrate the time-averaged magnetic moment 15 as a stationary upward magnetic moment 15a. The compressed precession waveform 56 which still retains the normal precession rate of the alkali gas 14 in the magnetic field $B_0$ boosts the length of the average magnetic moment 15 over that which might be provided by a sinusoidal $B_1$ field by a significant amount (for example 10 times) greatly increasing the effect on the noble gas 16. In addition, effective neutralization of the $B_0$ field during time 29 comprising most of the precession cycle, substantially reduces dephasing of the precession due to spin-exchange between atoms of the alkali gas 14. This stationary magnetic moment 15a represents moment experienced by the noble gas 16 during its precession during the irregular precession of the alkali gas 14, the latter of which generally has precession rate as much is 1000 times higher the precession rate of the noble gas 16.

Figure 4:
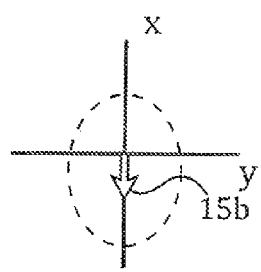
FIG. 4 is a graph and vector diagram similar to those of FIG. 14 and FIG. 13, showing a precession rate providing magnetic moment of the alkali gas having a time averaged downward vertical orientation.

Referring now to FIG. 4, it will be understood that the same waveform 56 with an inversion of signal 36 received by the polarization modulator 34 will produce a precession waveform 60 producing a time averaged magnetic moment 15b facing downward along the x-axis. Accordingly, by switching signal 36, an effective upward or downward magnetic moment 15a or 15b of the alkali gas 14 may be generated within the transverse x-y plane.

Figure 5:
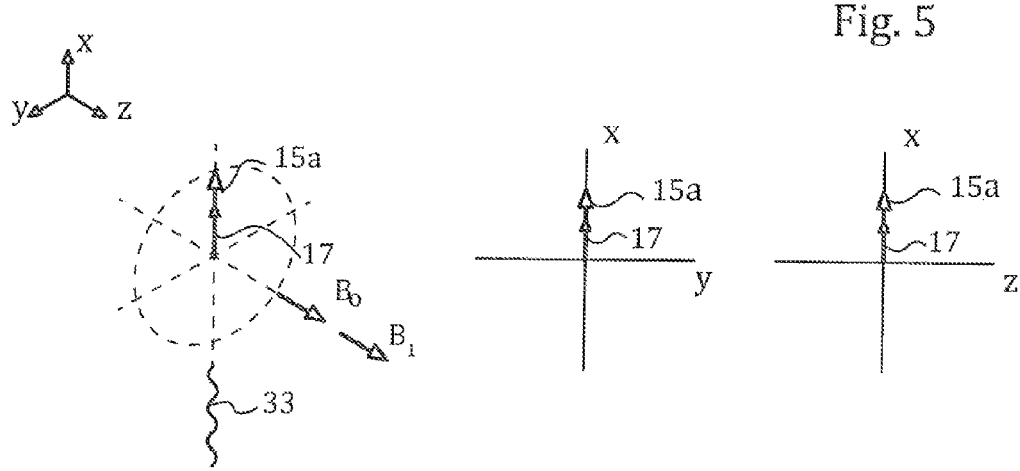
FIGS. 5-8 are corresponding perspective, x-y plane and x-z plane depictions of the magnetic moments of the noble gas and alkali gas during transverse plane precession of the magnetic moments of the noble gas population as induced by switching between the modulation patterns producing upward and downward magnetic moment for the alkali gas.
Figure 9:
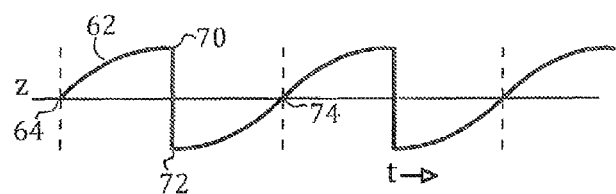
FIG. 9 is a plot of the signal received by a z-axis sensing laser such as provides a measure of precession of the noble gas about the z-axis.

Referring now to FIG. 5, the laser beam 33 from the pump laser 32 and the coils 23 initially may be modulated to produce the upward directed time averaged magnetic moment 15a causing the magnetic moments 17 of the population of noble gas to align therewith along the x-axis. Referring also to FIG. 9, at this time a z-component signal 62 from the first Faraday rotational probe 21 will show no z-axis component as indicated at waveform value 64.

Figure 6:
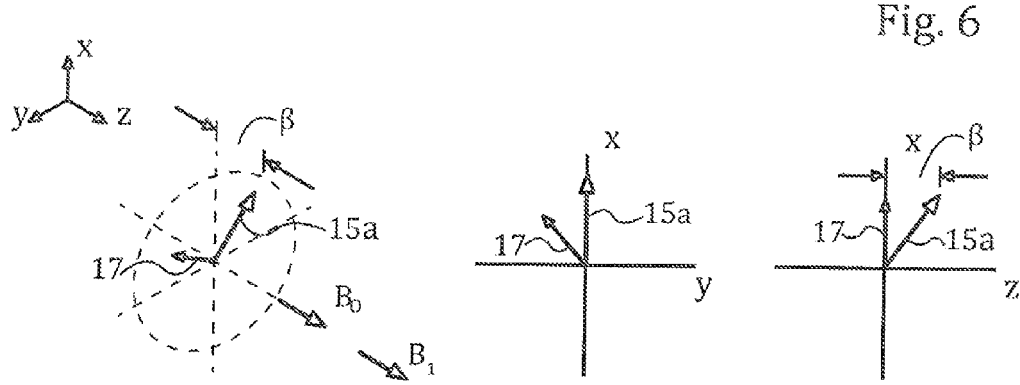

Referring now to FIG. 6, a short time later, the magnetic moments 17 of the noble gas will have precessed away from a vertical orientation along the x-axis caused by the influence of the external magnetic field $B_0$. The divergence of the magnetic moments 15a and 17 causes a torque on the magnetic moment 15a pushing the magnetic moment 15a by an angle β out of the x-y plane in the direction of $B_0$. This excursion of the magnetic moment 15a out of the x-y plane applies a slight additional z-axis magnetic field to the noble gas (adding to field $B_0$) causing the noble gas 16 to increase slightly in precession. A similar torque will be applied to the magnetic moment 17 which will be neglected at this time.

Figure 7:
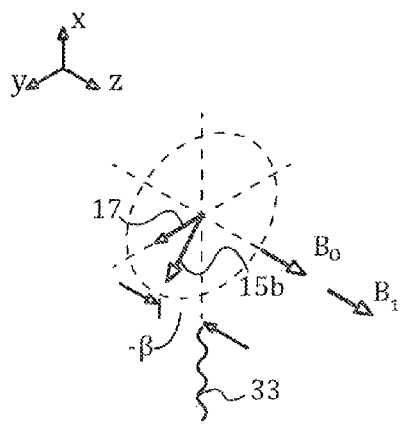
Figure 7:
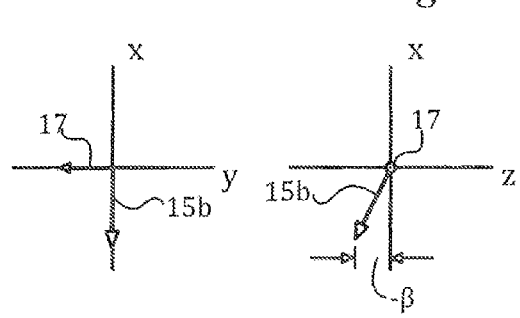

Referring now to FIG. 7, after an additional time, the magnetic moment 17 of the noble gas 16 will have precessed to be aligned with the y-axis so that the magnetic moments 15a and 17 are nearly perpendicular. In this state, the magnetic moment 17 produces its maximum torque on magnetic moment 15a, which will afterwards begin to decrease as the magnetic moment 17 passes below the y-axis. Referring to FIG. 9, accordingly, at this time the z-component signal 62 is at a maximum waveform value 70 of zero slope. This point of zero slope may be used to change the polarization of the laser beam 33 to change the asymmetrical angular rotation of the alkali gas 14 to the pattern shown in FIG. 4, with the result of flipping the angle of the magnetic moment 15a to 15b so that it is facing vertically downward as depicted in FIG. 7.

As shown in FIG. 9, at this time the z-component signal 62 is at a negative waveform value 72 caused by a corresponding reversal of the torque on magnetic moment 15b from magnetic moment 17 still on the y-axis. This torque now causes the magnetic moment 15a to be deflected by an angle −β from the x-y plane but in a direction counter to that of $B_0$. This negative deflection of the magnetic moment 15b produces a negative z-axis component that slows the precession of the magnetic moment 17 by an amount offsetting the previously described increase in precession, resulting in no net effect on the magnetic moment 17 by the magnetic moments 15a and 15b of the alkali gas 14.

Figure 8:
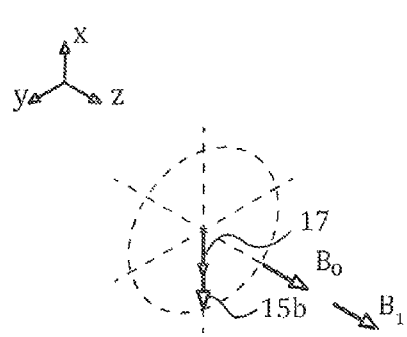
Figure 8:
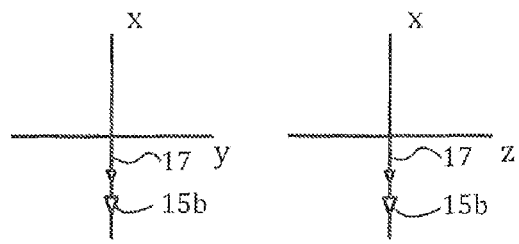

Referring now to FIG. 8, the magnetic moment 17 continues to precess until it is aligned with magnetic moment 15b directed downward along the x-axis. The torque between these magnetic moments 15b and 17 drops to zero. Referring to FIG. 9, z-component signal 62 returns to a zero value at waveform value 74.

It will be appreciated that the zero crossings 64 and 74 of waveform 62 may alternatively be used for synchronization of the modulation.

It will also be appreciated that the amount of deflection of the magnetic moment 15a and 15b out of the x-y plane is symmetrical not only in its peak value but also in its decline to have no net effect on the time average value of the precession of the magnetic moment 17.

Referring to FIG. 9, it will be understood that the periodicity of z-component signal 62 over one complete cycle represents the inverse of the precession frequency of the noble gas 16 without influence by the alkali gas 14 and can therefore be used to accurately measure the precession of the population of the noble gas 16 without additional sensing structure.

It should be noted that the magnetic moment 17 of the noble gas will also be affected by the torque caused by magnetic moments 15a and 15b of the alkali gas but again generally this deflection along the z-axis will be positive during a first-half cycle of the precession of the magnetic moment 15 and negative during a second-half cycle of that precession to be fully offset over one cycle.

Figure 10:
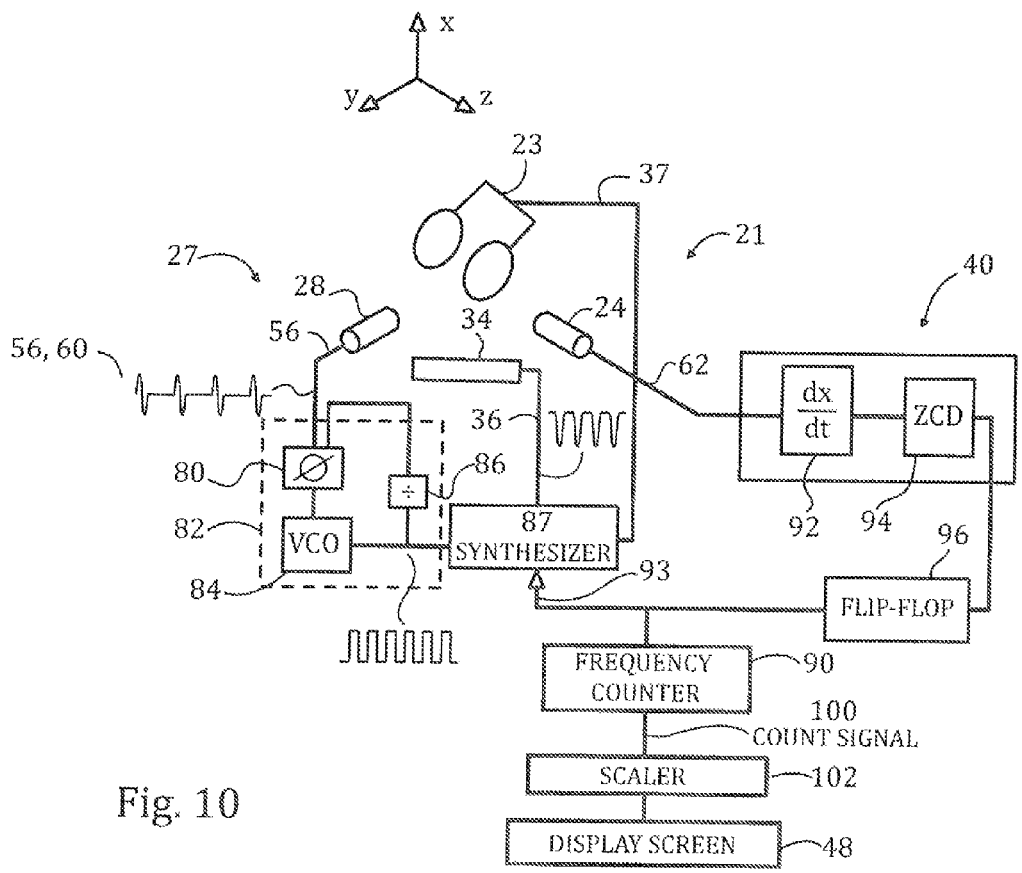
FIG. 10 is a functional block diagram of a control system for the present invention.

Referring now to FIG. 10, the control system 40 may implement a number of functional blocks either through discrete components or software or a combination of the same as described above. In one embodiment, precession waveform 56 from the polarimeter 28 representing the y-axis component of the precession of the alkali gas 14 may be received at a phase comparator 80 of a phase locked loop type lock-in amplifier 82. The phase comparator 80 may also receive an output of a voltage controlled oscillator 84 divided by a divider 86, and may operate to lock the phase and frequency of the voltage controlled oscillator 84 with the phase of the precession waveform 56 representing the precession of the magnetic moment 15 of the alkali gas 14.

The undivided high-frequency output of the voltage controlled oscillator may then be used to drive a synthesizer 87 synchronized to the precession waveform 56 providing a desired waveform implementing the modulation signal for driving the coils providing B1. The synthesized modulation signal 37 for coils 23 may be back-calculated from the desired precession waveforms 56 or 60, as will be understood by those of ordinary skill in the prior art, to maintain the time averaged alkali spin along the x-axis at substantially the frequency of the freely precessing alkali gas 14 in field $B_0$. Generally the amplifier 82 thus adjusts the phase and frequency of the synthesized modulation signal 37 for the coils 23 to match the natural precession frequency of the alkali gas 14

As noted, the synthesized modulation signal 36 may be selected to generate either the upward magnetic moment 15a or the downward magnetic moment 15b and this synthesized waveform may be selected by an input signal 93 to the synthesizer 87. This input signal 93 may be generated from the z-component signal 62 from polarimeter 24 of the first Faraday rotational probe 21 (shown in FIG. 9) by detecting the zero slope waveform value 70 of the positive peak of the z-component signal 62, for example, using a differentiator 92 and zero crossing detector 94 triggering a toggle or flip-flop 96. The flip-flop 96 provides a binary output producing the input signal 93 to switch the magnetic moment 15 of the alkali gas 14 appropriately using the polarization modulator 34.

In an alternative embodiment, the precession of the noble gas 16 may be measured directly using the Faraday rotational probe 27 which may be used to control the polarization modulator 34.

A frequency counter 90 may be used to produce a count signal 100 over a period of time, which may be scaled or otherwise processed by scaler 102 to provide for a display on display screen 48 indicating the precession frequency of the noble gas 16 or to provide the control output 50 for use as a gyroscope or magnetometer.

Figure 11:
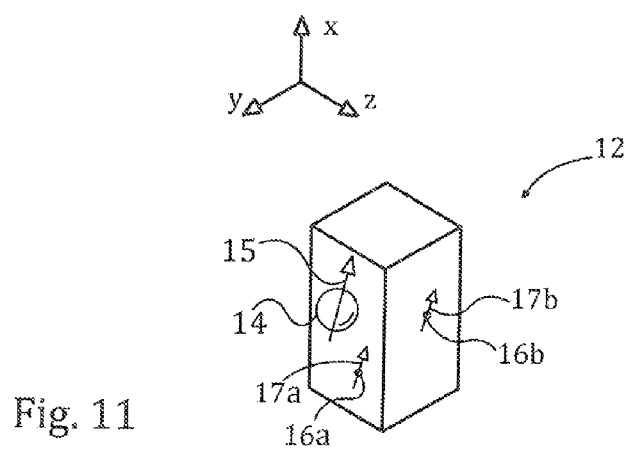
FIG. 11 is a representation of an alternative chamber of FIG. 1 holding multiple species of atoms for providing a gyroscope output less sensitive to the external magnetic field.

Referring now to FIG. 11, it will be appreciated that these principles and techniques described above may be extended to a chamber 12 holding a first and second isotope of noble gas 16a and 16b having magnetic moments 17a and 17b respectively with different gyromagnetic constants. The use of these two different isotopes permits the production of a control output 50 for a gyroscope that is largely indifferent to the value of the external magnetic field $B_0$ using the equations (1) (2) as discussed above. In such a system, the waveforms needed for each species of the isotope may be combined by multiplication and the sign of the product used to provide the signal to the polarization modulator 34. Frequency demultiplexing techniques may be used to extract the individual signals from the waveforms from the Faraday rotational probes 21 and 27. The control output 50 will then reveal the rotation of a coordinate system fixed with respect to the reference frame used to determine the precession of the noble gas 16, e.g. the reference frame of the Faraday rotational probe 21.

It will be appreciated that the present invention may be used, for example, with a magnetic shield 11 (shown in FIG. 1) to moderate the influence of external magnetic fields that may have variability, when a gyroscope is being constructed. In addition the invention may be used with nulling coils to provide a field $B_2$ generally aligned with the z-axis to null or control the $B_0$ field. The laser detectors shown may be replaced by other magnetic detectors including for example pickup coils. It will be understood that the gas mixtures described may include other gaseous elements and the invention may also use noble gases with quadrupole interactions. In addition it is contemplated that the invention may work in with hybrid spin-exchange optical pumping in which there are two species of alkali atoms and one interacts with the laser and the other works as a spin-bath to exchange angular momentum between the first alkali and the noble gas.

Alkali Gas Magnetometer

Figure 12:
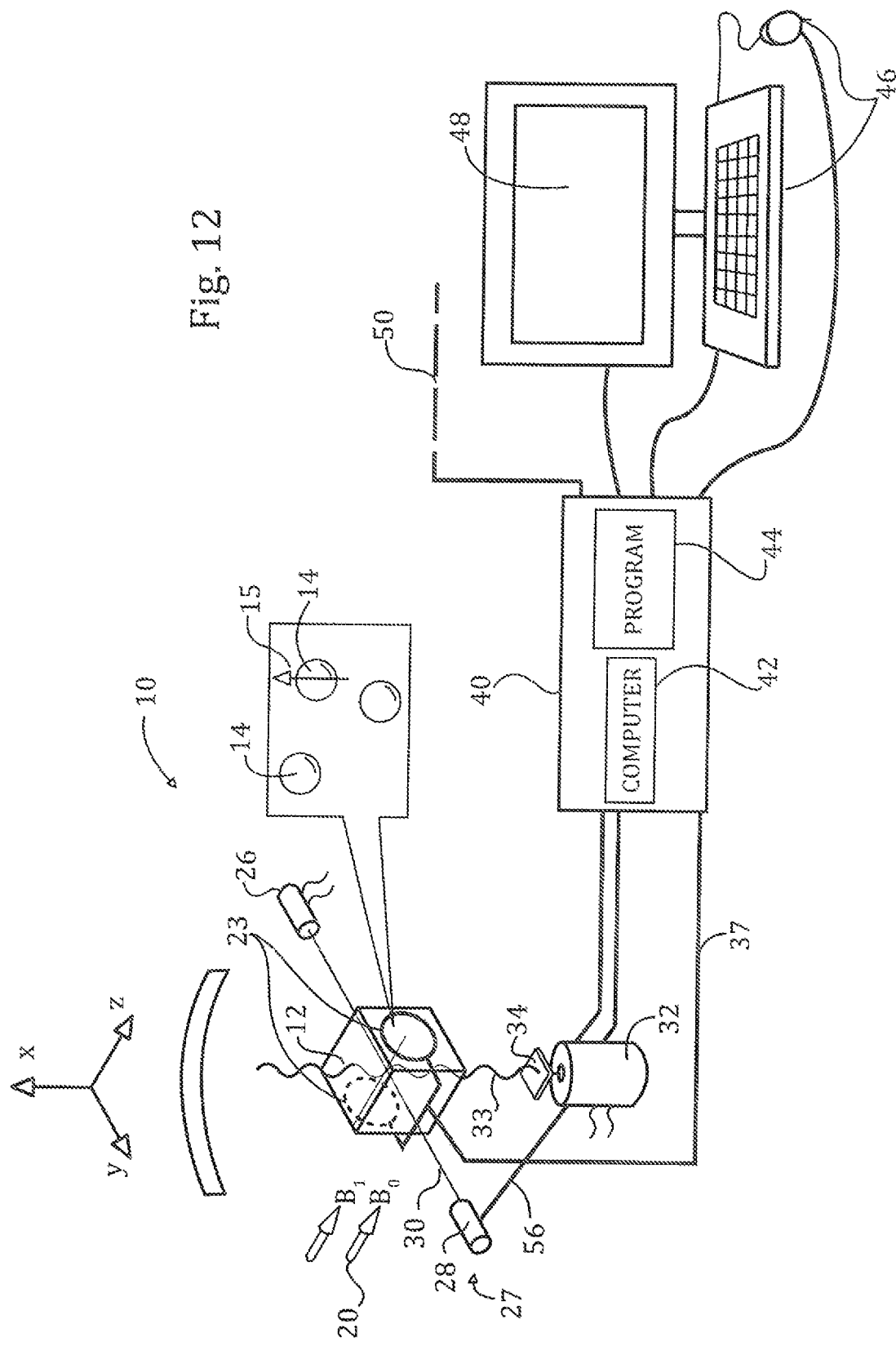
FIG. 12 is a figure similar to FIG. 1 showing a magnetometer of the present invention used, for example, with a single alkali gas species in contrast to the above described system using two gas species.

Referring now to FIG. 12, a magnetic resonator system 10, per another embodiment of the present invention, may include a chamber 12 holding as little as one species of alkali gas 14. In one embodiment, the alkali gas 14 may be rubidium (Rb). As discussed above, each of the atoms of the alkali gas 14 has a magnetic moment 17 represented by directional arrows in the figure.

A set of magnetic coils 23 (for example a Helmholtz coil pair flanking the chamber and aligned along the z-axis) may provide an alternating or pulsed magnetic field ($B_1$) aligned along the z-axis. As will be discussed below, this field provides a means for controlling the time-averaged alkali spin precession in the presence of an external field $B_0$. In particular, the field $B_1$ will be modulated to promote non-uniform precession to the alkali gas 14 in the external magnetic field $B_0$.

A Faraday rotational probe 27 may include a laser source 26 directing a laser beam 30 along the y-axis through the chamber 12 to a corresponding receiving polarimeter 28 on the other side of the chamber 12. This Faraday rotational probe 27 provides a measure of the y-axis component of the magnetic moment 15 of the population of alkali gas 14.

A "pump" laser 32 may direct a laser beam 33 along the x-axis through the chamber 12 after passing through a polarization filter 34. The pump laser 32 and polarization filter 34 may "spin-polarize" the magnetic moment 15 of the alkali gas 14 to align along the x-axis (upward as depicted). This polarization occurs by transfer of the angular momentum of the polarized photons of the laser beam 33 to the alkali gas 14

It will be understood that the various laser sources 26, and 32 in various combinations may be derived from one or more light sources.

Signals from the polarimeter 28 may be provided as an electrical signal input to a control system 40 to be processed as will be described below. The control system 40 may in turn output the modulation signal 37 to the magnetic coils 23. The control system 40 may be constructed of discrete components or functional blocks such as lock-in amplifiers, frequency counters and the like as will be described below or these elements may be implemented in software in an electronic computer 42 as depicted, or in dedicated hardware including an application-specific integrated circuit or digital signal processor, or as a combination of different elements in a hybrid configuration.

In the case of implementation in a computer 42, the computer 42 may execute a stored program 44 and may communicate with user input devices 46 such as a keyboard and/or mouse and may provide output for example through a graphic display screen 48 or other functionally similar device.

Figure 13:
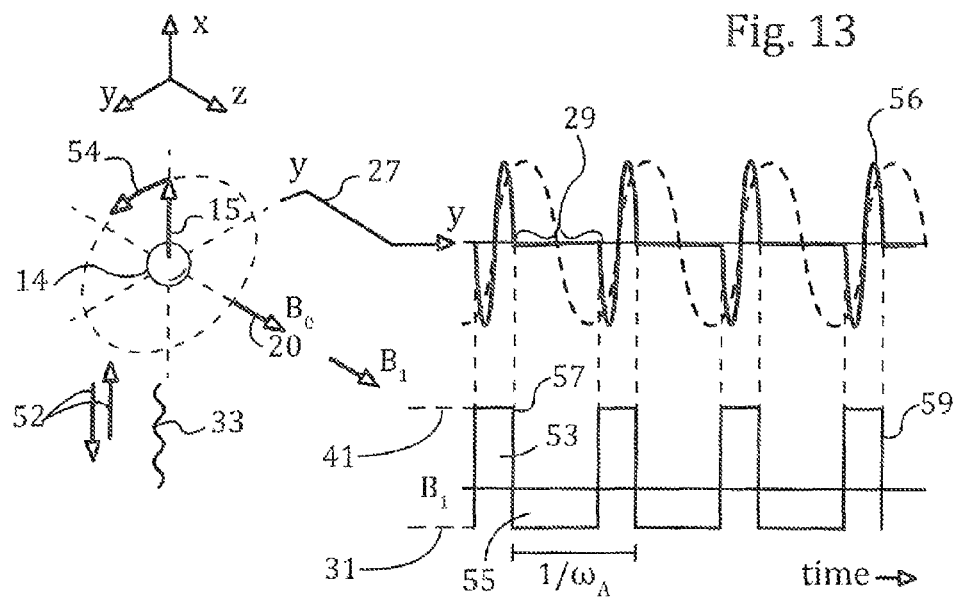
FIGS. 13-15 are figures similar to FIGS. 2-4 for the embodiment of FIG. 12.

Referring also to FIG. 13, during operation of the magnetic resonator system 10, the control system 40 will control the applied magnetic field $B_1$ to drive the magnetic moment of the population of alkali gas 14 into precession substantially within the x-y plane. This precession is invoked by illuminating the alkali gas 14 with photons having upward angular momentum indicated by arrow 52. The momentum of the photons is then transferred to the alkali gas 14 to align the magnetic moment 15 of the alkali gas 14 with the photons' angular momenta. Ongoing precession of the alkali gas 14 is then controlled by varying the $B_1$ field by control signal 37. The y-axis component of this precession of the magnetic moment 15 of the alkali gas 14 may be detected by the beam 30 of the Faraday rotational probe 27

The waveform of the $B_1$ field will be such that the precession 54 of the magnetic moment 15 of the alkali gas 14 in the x-y plane will not be at a uniform angular rate such as would be detected as a sinusoidal waveform by the Faraday rotational probe 27, but rather, as an irregular or non-uniform angular rate, progressing relatively slower in the upper half cycle such as will produce a compressed precession waveform 56. The compressed precession waveform 56 represents the y-axis component of an a precession having an angular rate with a greater dwell time 29 of the magnetic moment 15 of the alkali gas 14 during precession when the magnetic moment of the alkali gas 14 is facing in an upward rather than the downward direction.

This compressed precession waveform 56 may be produced by modulating the $B_1$ field signal 59 to a low relatively constant negative value 31 to substantially offset the $B_0$ field during the time 29 (greatly reducing the precession when the magnetic moment 15 is facing upward) for most of the period $2\pi/\omega$ of the normal precession of the alkali gas 14 in field $B_0$. The $B_1$ field signal 59 may then be maximized during a short time remaining in $2\pi/\omega$ by providing a positive pulse 57 of amplitude 41 augmenting the field $B_0$ to promote rapid precession of the alkali gas 14 by 360 degrees back to the upward orientation. The field $B_1$ signal 59 is controlled to have no direct current (that is areas 53 and 55 during times 29 and the remainder of $2\pi/\omega$ are equal and opposite) so that it has no net effect on the precession frequency of the alkali gas 14.

Figure 14:
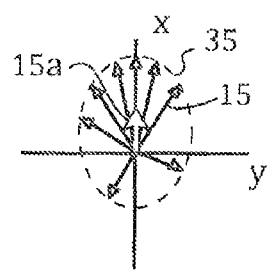

Referring momentarily to FIG. 14, a diagram of the alkali magnetic moment 15 at various points in time as an angular vector having a length proportional to the incremental dwell time at each angle, it traces an oval outline 35 reflecting the increased time weighting of the magnetic moment in the upward direction. The centroid of this outline 35 may illustrate the time-averaged magnetic moment 15 as a stationary upward magnetic moment 15a. The effective neutralization of the $B_0$ field during time 29, comprising most of the precession cycle, substantially reduces dephasing of the precession due to spin-exchange between atoms of the alkali gas 14.

Figure 15:
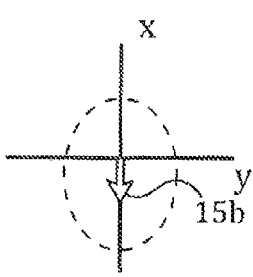

Referring now to FIG. 15, it will be understood that the same waveform 56 with an inversion of signal 36 received by the polarization modulator 34 will produce a precession waveform 60 producing a time averaged magnetic moment 15b facing downward along the x-axis. Accordingly, by replacing the polarization filter 34 with a polarization modulator, an effective upward or downward magnetic moment 15a or 15b of the alkali gas 14 may be generated within the transverse x-y plane. This switching of polarity may be useful for the measurement of AC magnetic fields.

Figure 16:
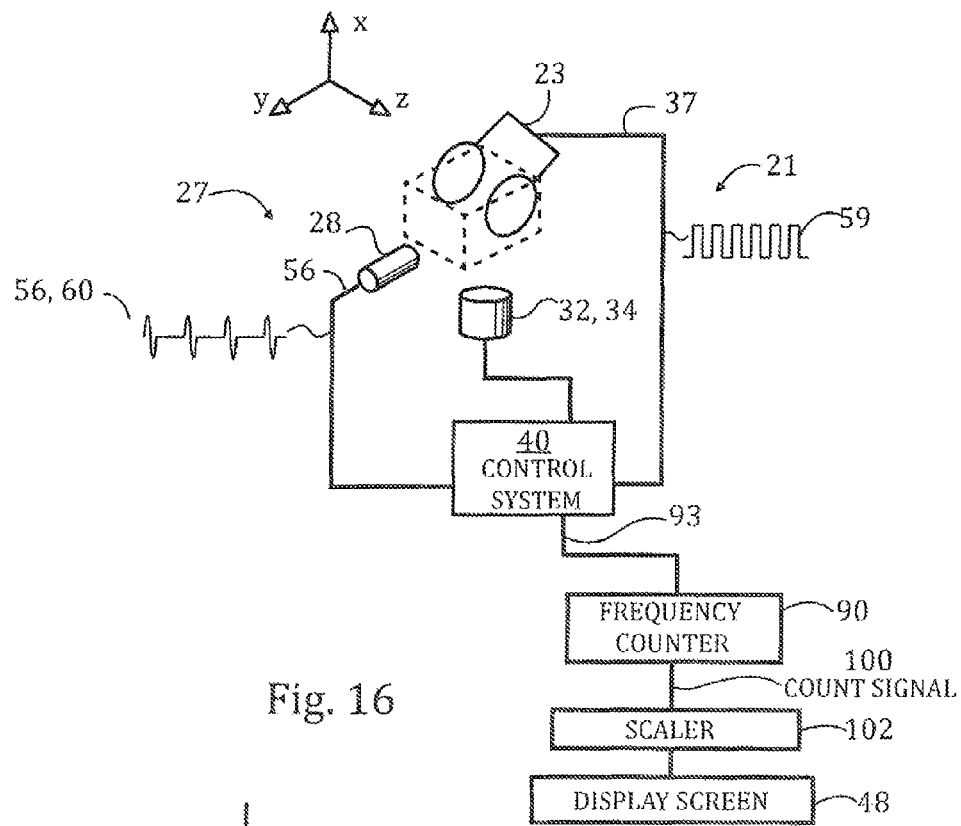
FIG. 16 is a figure similar to FIG. 10 for the embodiment of FIG. 12.

Referring now to FIG. 16, the control system 40 may implement a number of functional blocks either through discrete components or software or a combination of the same as described above. In one embodiment, precession waveform 56 from the polarimeter 28 representing the y-axis component of the precession of the alkali gas 14 may be received at the control system 40 The control system 40 also synthesizes the driving signal 37 providing field signal 59 to the magnetic coils 23.

Figure 17:
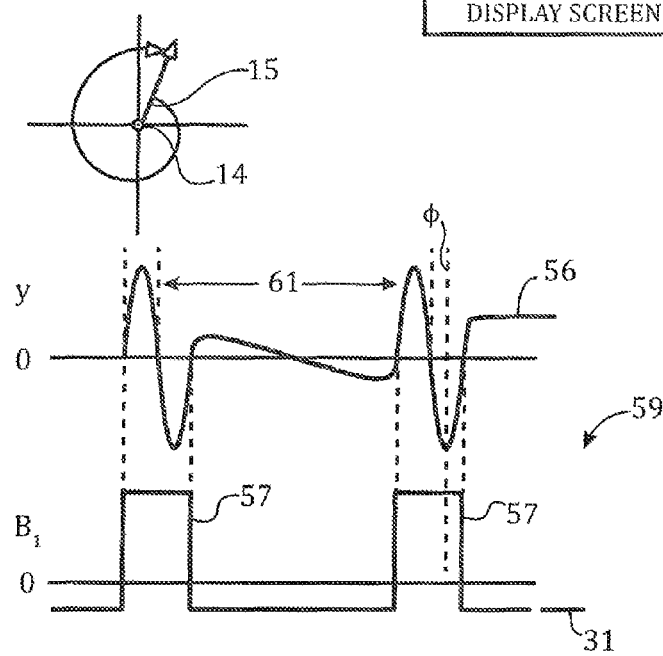
FIG. 17 is a figure similar to FIG. 2 for the embodiment of FIG. 12 showing phase sensitive feedback for control of pulse width.

Referring now to FIGS. 16 and 17, the control system 40 monitoring the precession waveform 56 from the polarimeter 28 may control the frequency of the pulse 57 to ensure proper alignment of the magnetic moment 15 along the x-axis. One way to accomplish this is to monitor the zero crossing of the signal 56 with respect to the width or beginning of the pulses 57. When the pulse width 57 is correct, the zero crossing of signal 56 will will have a period 61 such that it will bisect the pulse 57 in time (for an integer multiple of 360 degrees of precession during the pulse 57). When the area of the pulse 57 is too great (as shown in FIG. 17) the magnetic moment 15 will overshoot the x-axis during the precessing cycle (greater than an integer number of revolutions), advancing the phase of the succeeding waveform at the next pulse 57 by a phase error $\Delta\phi$. This phase error $\Delta\phi$ may be readily detected by the control system 40 to decrease the pulse width 57 by synthesis techniques well known in the art and to be discussed below. Conversely, it will be understood that if the pulse width 57 is too narrow, the magnetic moment 15 will undershoot the x-axis during the precessing cycle (less than an integer number of revolutions) causing a detectable delay in the zero crossing of the waveform 56 (not shown) effecting the opposite correction.

The control system also monitors the time-average of the detected waveform 56 from the Faraday probe. The repetition period of the waveform 57 of $B_1$ is adjusted to hold the time-averaged value of waveform 56 to be zero. Then the frequency is precisely equal to the mean Larmor precession frequency in the field $B_0$. This frequency may be used to deduce the strength of the external magnetic field.

It will be understood that the level 31 of the waveform 59 may be independently adjusted within this control strategy to decrease the width of the pulses 57 and thus increase the time during which the atoms 14 are subject to substantially zero total field ($B_1$ plus $B_0$) as desired. Generally, the duty cycle of the pulses 57 (that is the ratio of their width to the period of the precessing cycle measured pulse to pulse) will be much less than 50 percent of the cycle and more typically much less than 10 percent of the cycle and ideally will be minimized within the practical constraints of the apparatus.

It will be understood then, that the field signal 59 will in this way be synchronized to the precession waveform 56 while maintaining the time averaged alkali spin along the x-axis at substantially the frequency of the freely precessing alkali gas 14 in field $B_0$. Generally, the control system 40 thus adjusts the phase and frequency of the synthesized modulation signal 37 as well as the area 53 relative to area 55 for the coils 23 to match the natural precession frequency of the alkali gas 14.

A frequency counter 90 may be used to produce a count signal 100 over a period of time, which may be scaled or otherwise processed by scaler 102 to provide for a display on display screen 48 indicating the precession frequency of the alkali gas 14 indicating magnetic field strength of $B_0$.

It will be appreciated that the control system 40 as described above may be replaced with a simple manual adjustment system in cases where the external magnetic field is largely static. In such a system, the signal from the Faraday probe 27 would be observed and the signal 59 adjusted to provide the desired phasing and average value. The frequency of the signal from the Faraday probe 27 would then be used to deduce magnetic field strength. Another way to implement a magnetometer applied field $B_1$ as described above and to provide a feedback magnetic field $B_2$ that works to maintain a constant value of $B_0+B_2$ to maintain resonance.

It will be appreciated that the present invention may be used in all of these embodiments, for example, with a magnetic shield 11 (a fragment shown in FIGS. 1 and 12) to moderate the influence of external magnetic fields that may have variability. In addition the invention may be used with nulling coils to provide a field $B_2$ generally aligned with the z-axis to null or control the $B_0$ field. The laser detectors shown may be replaced by other magnetic detectors including for example pickup coils. It will be understood that the gas described may include other gaseous elements including for example other alkali gases or metastable helium or the like. A hybrid spin-exchange optical pumping mixture may be used using for polarizing the gases, for example, using two species of alkali atoms.

An embodiment of the magnetometer that is appropriate to measure AC magnetic fields at a frequency f can be realized by applying a static field $B_0=f_0/\gamma$, the modulating field $B_1$ at frequency $f_1$, and additionally modulating the pump laser polarization at the frequency $f=f_0-f_1$. This produces a rotating polarization of the spins at frequency f. A second Faraday probe added along the z direction then detects a DC rotation for AC fields that are orthogonal to the rotating spin polarization.

Generally, the term "magnetic field" as used herein should be understood to refer to both or either of the classical magnetic field and a quantum mechanical term that looks like a magnetic field, as context would require. The terms "alkali" and "alkali gas" as used herein should be understood to refer to "alkali-metal atom" or "alkali-metal gas" or "alkali-metal magnetic moment" as context would require per the understanding of those of ordinary skill in the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a controller" and "a processor" or "the microprocessor" can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A magnetometer comprising:
    a chamber holding a gas exposable to an external magnetic field other than that generated locally by the magnetometer and directed along a z-axis;
    an electromagnet positioned to apply a local magnetic field to the chamber;
    a signal source communicating with the electromagnet and generating a field signal adapted to drive the electromagnet to produce a local magnetic field causing a non-uniform precession of a magnetic moment of the gas limiting a portion of each cycle of the field signal during which substantial precession occurs; and
    a detector measuring a frequency of the non-uniform precession of the magnetic moment to provide an output indicating a strength of the external magnetic field.

2. The magnetometer of claim 1 wherein the signal is adapted to limit the portion of each cycle of the field signal during which substantial precession occurs to less than 50% of the cycle.

3. The magnetometer of claim 2 wherein the signal is adapted to limit the portion of each cycle of the field signal during which substantial precession occurs to less than 10% of the cycle.

4. The magnetometer of claim 1 further including:
    a precession monitor providing a moment signal indicating orientation of a magnetic moment of the gas in the chamber; and
    a feedback control system receiving the moment signal to control the signal from the signal source to complete substantially an integer multiple of 360 degrees of precession of the gas during the portion of each precession cycle during which substantial precession occurs.

5. The magnetometer claim 4 wherein the feedback control system monitors a phase of the moment signal to control the field signal.

6. The magnetometer of claim 1 wherein the field signal has an average signal value of substantially zero.

7. The magnetometer of claim 6 further including a laser modulating the polarity of the magnetic moment of the gas at a laser modulation frequency and wherein the detector provide an output indicating a strength of the external magnetic field as a function of the frequency of the field signal and of the laser modulation frequency.

8. The magnetometer of claim 1 wherein the gas is an alkali gas.

9. The magnetometer of claim 1 wherein the gas is metastable Helium.

10. A magnetometer comprising:
    a chamber holding a gas exposable to an external magnetic field other than that generated by the gas and directed along a z-axis;
    an electromagnet positioned to apply a local magnetic field to the chamber;
    a signal source providing a field signal to the electromagnet having substantially a zero average value and adapted to substantially cancel to a value of zero a total external magnetic field experienced by the gas during at least one half a cycle of the field signal; and
    a detector monitoring at least one of a phase and frequency of the precession of the magnetic moments of the gas to control the field signal and to output an indication of a strength of the external magnetic field.

11. The magnetometer of claim 10 wherein the signal is adapted to substantially cancel to a value of zero the magnetic field during at least 90 percent of the cycle of a field signal.

12. The magnetometer of claim 10 wherein the gas is an alkali gas.

13. The magnetometer of claim 10 wherein the gas is selected from the group consisting of rubidium and metastable Helium.

14. The magnetometer of claim 10 further including:
   a precession monitor providing a moment signal indicating orientation of a magnetic moment of the gas in the chamber; and
   a feedback control system receiving the moment signal to control the field, signal from the signal source to produce substantially an integer multiple of 360 degrees of precession during a portion of the field signal when the total external magnetic field experienced by the gas is not substantially zero.

15. The magnetometer claim 14 wherein the feedback control system monitors a phase of the moment signal to control the field signal.

16. The magnetometer of claim 10 wherein the field signal has an average signal value of substantially zero.

17. The magnetometer of claim 16 further including a laser modulator controlling polarization of the magnetic moments of the gas at a laser modulation frequency and the detector provides an output indicating a strength of an external AC magnetic field oscillating at the laser modulation frequency.

18. A method of measuring magnetic fields comprising the steps of:
   (a) exposing a gas to a magnetic field external to that generated by the gas and directed along a z-axis;
   (b) applying a local magnetic field to produce a non-uniform precession of a magnetic moment of the gas about the z-axis while limiting a portion of each precession cycle during which substantial precession occurs; and
   (c) monitoring the non-uniform precession of the magnetic moment to provide an output indicating a strength of the external magnetic field.

19. A method of measuring an oscillating magnetic field comprising the steps of
   (a) exposing a gas having a gyromagnetic constant of $\gamma$ to a static local magnetic field $B_0$;
   (b) exposing the gas to a magnetic field $B_1$ varying at a frequency $f_1$;
   (c) modulating a laser to polarize the has at a frequency $f_2 = B_0\gamma - f_1$; and
   (d) detecting a precession frequency indicating a presence of a weak AC magnetic field at or near a frequency $f_2$.

* * * * *